United States Patent
Dumont

(10) Patent No.: US 10,963,672 B2
(45) Date of Patent: Mar. 30, 2021

(54) METHOD FOR DETECTING THE PRESENCE OF A BODY PART CARRYING AN IMPRINT ON A IMPRINT SENSOR

(71) Applicant: IDEMIA IDENTITY & SECURITY FRANCE, Issy les Moulineaux (FR)

(72) Inventor: Denis Dumont, Issy les Moulineaux (FR)

(73) Assignee: IDEMIA IDENTITY & SECURITY FRANCE, Issy les Moulineaux (FR)

( * ) Notice: Subject to any disclaimer, the term of this patent is extended or adjusted under 35 U.S.C. 154(b) by 100 days.

(21) Appl. No.: 16/156,773

(22) Filed: Oct. 10, 2018

(65) Prior Publication Data
US 2019/0108382 A1 Apr. 11, 2019

(30) Foreign Application Priority Data

Oct. 11, 2017 (FR) ..................................... 17/59524

(51) Int. Cl.
*G06K 9/00* (2006.01)
*A61B 5/1172* (2016.01)
*G06K 9/20* (2006.01)

(52) U.S. Cl.
CPC .......... *G06K 9/0012* (2013.01); *A61B 5/1172* (2013.01); *G06K 9/00046* (2013.01); *G06K 9/2018* (2013.01)

(58) Field of Classification Search
CPC ............. G06K 9/00046; G06K 9/2018; G06K 9/00–82; G06K 9/00006–00093; G06K 9/52–527; G06K 9/0012; A61B 5/1172
USPC .................................................. 382/124–127
See application file for complete search history.

(56) References Cited

U.S. PATENT DOCUMENTS

| | | | | |
|---|---|---|---|---|
| 2005/0013486 A1* | 1/2005 | Wiedemann | .......... | G06K 9/6857 382/181 |
| 2011/0211055 A1* | 9/2011 | Martin | ............... | G06K 9/00033 348/77 |
| 2013/0258086 A1* | 10/2013 | Erhart | ................ | H04N 5/23219 348/77 |

FOREIGN PATENT DOCUMENTS

| | | |
|---|---|---|
| EP | 1 810 221 A1 | 7/2007 |
| FR | 2 915 008 A1 | 10/2008 |
| WO | 2006/074407 A2 | 7/2006 |

OTHER PUBLICATIONS

Jul. 6, 2018 Search Report issued in French Patent Application No. 17/59524.

* cited by examiner

*Primary Examiner* — Amr A Awad
*Assistant Examiner* — Aaron Midkiff
(74) *Attorney, Agent, or Firm* — Oliff PLC; R. Brian Drozd

(57) ABSTRACT

Method for detecting the presence of a body part carrying an imprint on an imprint sensor comprising a transparent face on which a body part must be placed, an image sensor, situated opposite the transparent face, able to acquire an image of an imprint, a light source for illuminating a body part placed on the transparent face. The method comprises: switching on the light source; acquiring a multicomponent image with the image sensor, each color component of the multicomponent sensor corresponding to a predefined wavelength range; obtaining, for each color component of said multicomponent image, information representing a signal generated by said image sensor for said color component; comparing said representative items of information with each other and detecting the presence of a body part according to the result of the comparison.

5 Claims, 4 Drawing Sheets

METHOD FOR DETECTING THE PRESENCE OF A BODY PART CARRYING AN IMPRINT ON A IMPRINT SENSOR

The invention relates to a method for detecting the presence of a body part carrying an imprint on an imprint sensor and a device implementing the method.

CONTEXT OF THE INVENTION

The use of imprints, for example of prints of a finger, of a plurality of fingers, or of the palm of a hand, allows to protect access to buildings or machines. Such technology allows to dispense with access codes or cards, which may be borrowed, stolen or falsified. The use of this technology reinforces security since the probability that two persons have two identical imprints is almost zero.

A device for capturing an imprint allows to capture an image of an imprint. In the case of identification, this imprint is compared with a set of reference imprints contained in a database. In the case of authentication, this imprint is compared with a single imprint. The comparison allows to determine whether or not the imprint captured belongs to a person referenced in the database or whether the person is indeed the one that he claims to be FIG. 1 describes schematically a device for capturing a fingerprint using the principle of total reflection and able to function on a light field or on a dark field.

The device 10 described in FIG. 1 comprises a prism 100, two light sources 101A and 101B, and an optical system 102 such as for example a CCD (charge-coupled device) image sensor or CMOS (complementary metal oxide semiconductor) image sensor and one or more lenses.

The light source 101A generates a light beam that passes through a first face 100A of the prism 100 as far as a second face 100C of the prism 100, where a body part is positioned, carrying a fingerprint (here a finger D). The fingerprint consists of valleys and ridges. The light beam generated by the light source 101A forms an incident angle $\alpha_A$ to the normal of the face 100C. The angle $\alpha_A$ is larger than a critical angle $\theta_c$ and smaller than a limit angle $\theta_l$.

The face 100C separates a first medium corresponding to the prism 100 from a second medium corresponding to the air or to the finger D. The critical angle $\theta_c$ (or respectively the limit angle $\theta_l$) is defined as an angle beyond which total reflection occurs when a beam reaches the face 100C when the second medium is air (or respectively when the second medium is the finger D).

When the finger D is placed on the face 100C, the light beam generated by the light source 101A undergoes total reflection when, at the position struck by the light beam on the face 100C, the finger forms a valley, i.e. there is air between the face 100C and the finger D. When, at the position struck by the light beam on the face 100C, the finger forms a ridge, i.e. the skin of the finger is in direct contact with the face 100C, there is no total reflection. The total reflection is then said to be frustrated and the light beam is diffused in the finger D.

After reflection on the face 100C, the light beam passes through the fourth face 100D and reaches the optical system 102. The optical system 102 then forms an image of the fingerprint with a high contrast between the valleys and ridges. The valleys correspond to beams totally reflected by the face 100C and therefore appear to be very bright in the image. The ridges correspond to diffused light beams, partly absorbed in the finger D, which have re-emerged from the finger in order to reach the optical system 102. The ridges therefore appear darker in the image.

The optical system 102 therefore receives the light beams both reflected by the face 100C and diffused in the finger D. The device formed by the light source 101A, the prism 100 and the optical system 102 is a device using the principle of total reflection with light-field. A similar device can be found in the American patent U.S. Pat. No. 3,200,701.

The device formed by the light source 101B, the prism 100 and the optical system 102 functions according to a different principle. The light source 101B generates a light beam that passes through a third face 100B of the prism 100 as far as the second face 100C, where the finger D is positioned. The light beam generated by the light source 101B forms an incident angle $\alpha_B$ with the normal to the face 100C less than the critical angle $\theta_c$ (here the incident angle $\alpha_B$ is of zero degrees). There is therefore no total reflection of the rays from the source 101B in this case, this source being used for illuminating the finger D.

The optical system 102 therefore receives the light beam generated by the light source 101B after diffusion by the finger D. The optical system 102 is configured so as to receive light beams after diffusion in the finger D forming an angle lying between the critical angle $\theta_c$ and the limit angle $\theta_l$ with the normal to the face 100C. There also, the optical system 102 forms an image of the fingerprint with a high contrast between the valleys and ridges. The ridges correspond to light beams diffused by the finger D and which have re-emerged from the finger at the ridges in contact with the face 100C in order to reach the optical system 102. No light beam diffused in the finger D and emerging from the finger D at the valleys can reach the optical system 102 since they cannot pass through the layer of air and then propagate in the prism 100 while forming an angle with respect to the normal to the face 100B greater than the critical angle $\theta_c$. The ridges therefore appear brighter in the image of the fingerprint than the valleys. The device formed by the light source 101B, the prism 100 and the optical system 102 is a device using the principle of total reflection with dark-background. A similar device can be found in the French patent FR 2757974.

The critical angle $\theta_c$ is given by the following formula:

$$\theta_c = \arcsin\left(\frac{n_0}{n_1}\right)$$

$n_1$ being the refractive index of the prism and $n_0$ being the refractive index of the air or finger. For a refractive index of the air equal to "1" and a refractive index of the prism equal to "1.5", a critical angle $\theta_c$=41.8 degrees is obtained. The refractive index of the skin is, in the visible domain, between 1.41 and 1.47. Considering the minimum value of "1.41", a limit angle $\theta_l$ of "70" degrees is therefore obtained. Considering the maximum value, an angle $\theta_l^{max}$ of "76" degrees is obtained.

A function of detection of the presence of body parts is generally associated with a fingerprint sensor in order to trigger processing when a body part is detected as being placed on the fingerprint sensor. The presence detection function is sensitive since it must not trigger processing in the presence of a trace on the fingerprint sensor. Such trace (dirt, sweat or other residues), also referred to as a latent, may have been left by previous applications of a finger on the fingerprint sensor. It is known that traces may generate information similar to certain types of body part such as dry fingers. It then becomes difficult to distinguish dry fingers from latents. This problem is in particular encountered by fingerprint sensors using optical acquisition technology such as sensors using the principle of total reflection with dark-field or light-field described in relation to FIG. 1.

In order to distinguish a body part placed on a fingerprint sensor from a latent, producing a first image with a light source of the fingerprint sensor switched on and a second image with light source switched off is known. This method is slow since it requires two image acquisitions and does not function in the case of strong ambient light (for example in sunlight).

It is desirable to overcome these drawbacks of the prior art. It is in particular desirable to propose a method and device that allows to better distinguish a latent from a finger, including in the presence of a dry finger. Moreover, this method must be simple to implement.

DISCLOSURE OF THE INVENTION

According to a first aspect of the invention, the invention relates to a method for detecting the presence of a body part carrying an imprint on an imprint sensor comprising a transparent face on which a body part must be placed, an image sensor, situated opposite the transparent face, able to acquire an image of a imprint, a light source for illuminating a body part placed on the transparent face. The method comprises: switching on the light source; obtaining a multicomponent image from the image sensor, each colour component of the multicomponent sensor corresponding to a predefined wavelength range; obtaining, for each colour component of said multicomponent image, an item of information representative of a signal generated by said image sensor for said colour component; comparing said representative items of information with each other and detecting the presence of a body part according to the result of the comparison.

The invention allows, from a single acquisition of images and taking advantage of the different properties of reflection, diffusion and absorption of a body part, to quickly and simply identify the presence of a body part on an image sensor. Thus it is simpler to distinguish between a latent and a dry finger.

According to one embodiment, the image sensor directly supplies a multicomponent image or successively supplies mono-component images each corresponding to a predefined wavelength range, the mono-component images forming the multicomponent image.

According to one embodiment, the imprint sensor functions according to a total reflection with dark-field principle, and the light source produces light the wavelengths of which lie solely in one of the predefined wavelength ranges, referred to as the illuminating wavelength range. The method comprises: forming a mono-component image from each component of the multicomponent image and determining a value representing each mono-component image; comparing the representative values of each component with each other, and detecting the presence of a body part when a difference between the representative value determined for the colour component corresponding to the illuminating wavelength range and the other representative values is above a predetermined threshold.

According to one embodiment, the imprint sensor functions according to a total reflection with dark-field principle, the light source produces light the wavelengths of which are situated in a first predefined wavelength range and in at least one second predefined wavelength range, and the method comprises: obtaining from the image sensor a first mono-component image comprising the component of the multi-component image corresponding to the first predefined wavelength range and for each second predefined wavelength range a second mono-component image comprising the component of the multicomponent image corresponding to said second predefined wavelength range, each mono-component image being an item of information representing a signal generated by said image sensor for a colour component; calculating a difference image between the first image and each second image and between each second image; determining a value representing each difference image, detecting the presence of a body part when at least one of the representative values is above a first predetermined threshold.

According to one embodiment, the imprint sensor functions according to a total reflection with light-field principle, the light source produces light the wavelength of which is situated in a first predefined wavelength range and in at least one second predefined wavelength range, and the method comprises: obtaining from the image sensor a first mono-component image comprising the component of the multi-component image corresponding to the first predefined wavelength range and, for each second predefined wavelength range, a second mono-component image comprising the component of the multicomponent image corresponding to said second predefined wavelength range; calculating a value representing each mono-component image; comparing the representative values associated with each component with each other, detecting the presence of a body part when a difference between the representative value associated with the first monocomponent image and each representative value associated with a second monocomponent image is above a first predefined threshold.

According to one embodiment, the first component is a red component and each second component is a green or blue component.

According to a second aspect of the invention, the invention relates to a device for detecting the presence of a body part carrying an imprint on a imprint sensor comprising a transparent face on which a body part must be placed, an image sensor, situated opposite the transparent face, able to acquire an image of a imprint, and a light source for illuminating a body part placed on the transparent face. The device comprises: switching-on means for switching on the light source; obtaining means for obtaining a multicomponent image of the image sensor, each component of the multicomponent image corresponding to a predefined wavelength range; obtaining means for obtaining, for each colour component of said multicomponent image, an item of information representing a signal generated by said image sensor for said colour component; comparison means for comparing said representative items of information with each other and detecting the presence of a body part according to the result of the comparison.

According to a third aspect of the invention, the invention relates to an imprint sensor comprising a device according to the second aspect.

According to a fourth aspect of the invention, the invention relates to a computer program comprising instructions for the implementation, by a device, of the method according to the first aspect, when said program is executed by a calculation unit of said device.

According to a fifth aspect of the invention, the invention relates to storage means storing a computer program comprising instructions for the implementation, by a device, of the method according to the first aspect, when said program is executed by a calculation unit of said device.

BRIEF DESCRIPTION OF THE DRAWINGS

The features of the invention mentioned above, as well as others, will emerge more clearly from a reading of the following description of an example embodiment, said description being given in relation to the accompanying drawings, among which.

DETAILED DESCRIPTION OF VARIOUS EMBODIMENTS

Figure 1:
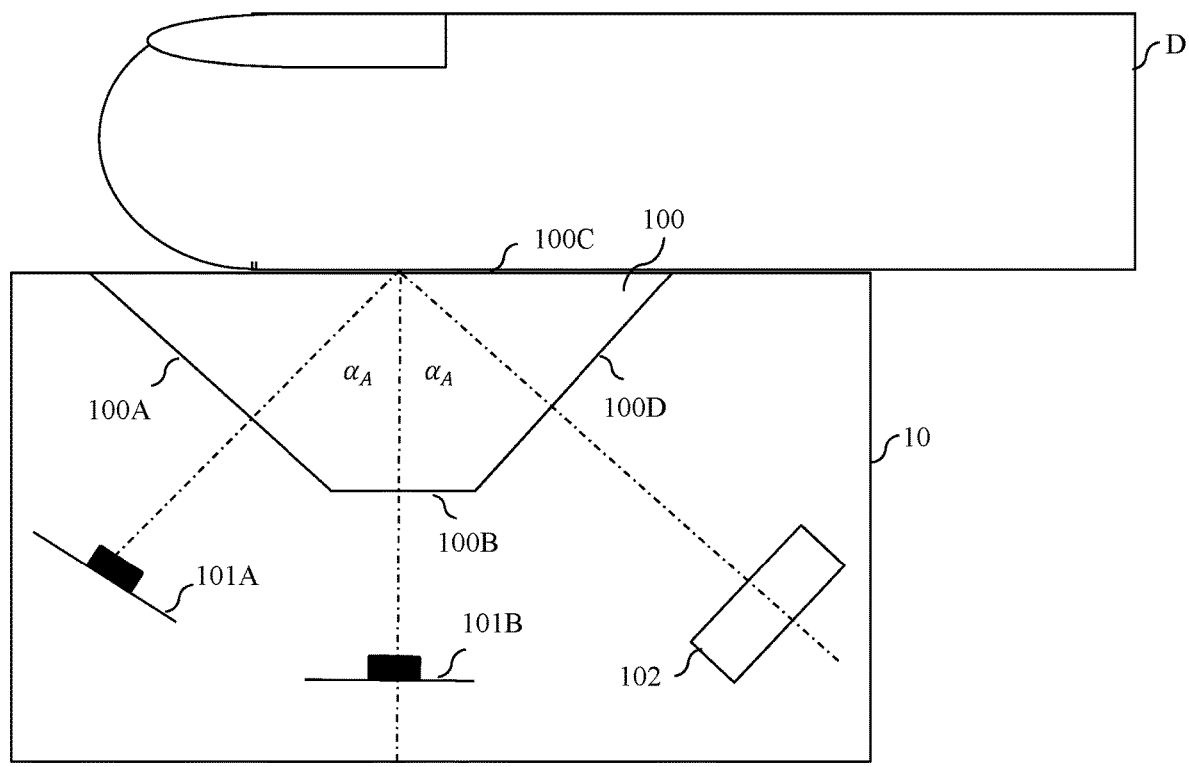
FIG. 1 describes schematically an imprint capture device of the prior art working in total reflection and able to function on a light field or a dark field.

The following description details more particularly embodiments of the present invention in a context of a fingerprint sensor used in equipment for controlling access to a room or a building. The invention can apply to other equipment that may comprise a device for capturing an imprint of a body part such as a computer, a tablet, a Smartphone, etc. Moreover, the invention is described in a context where the body part is a finger. It applies however to other body parts such as a plurality of fingers, the palm of a hand, etc. Furthermore, we describe the invention in a context where the fingerprint capture device is the one described in relation to FIG. 1. Other types of imprint sensor may be used and in particular imprint sensors in which the prism 100 is replaced by a transparent sheet.

Figure 2:
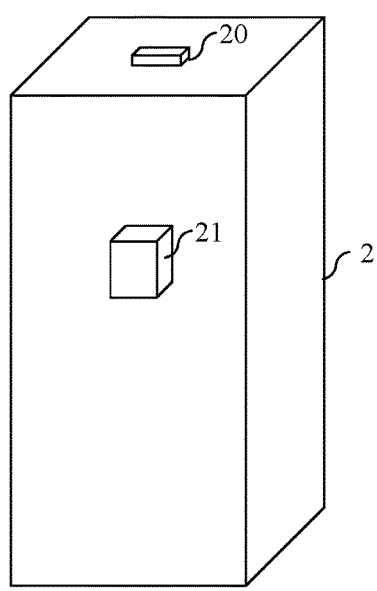
FIG. 2 illustrates schematically equipment comprising a fingerprint capture device according to the invention.

FIG. 2 illustrates schematically equipment comprising a fingerprint capture device according to the invention.

The equipment 2 is an access control equipment taking the form of a rectangular terminal comprising on a top face a fingerprint capture device 20. When a user wishes to access a room or a building, he places a finger on the fingerprint sensor 20. The fingerprint sensor 20 triggers the opening of a door when the user is recognised. The fingerprint sensor 20 is for example the one described in relation to FIG. 1. We assume hereinafter that each light source 101A and 101B produces light having a uniform power in all wavelengths captured by the optical system 102. Likewise, it is considered hereinafter that the optical system 102 has identical sensitivity for each wavelength received. If this were not the case, it would be preferable to rebalance each component produced by the optical system 102 so that they are comparable with each other. As we describe hereinafter, in certain embodiments this fingerprint sensor 20 uses the total reflection with light-field principle and in others the total reflection with dark-field principle. The equipment 2 comprises a processing module 21 able to implement the method according to the invention.

Figure 3:
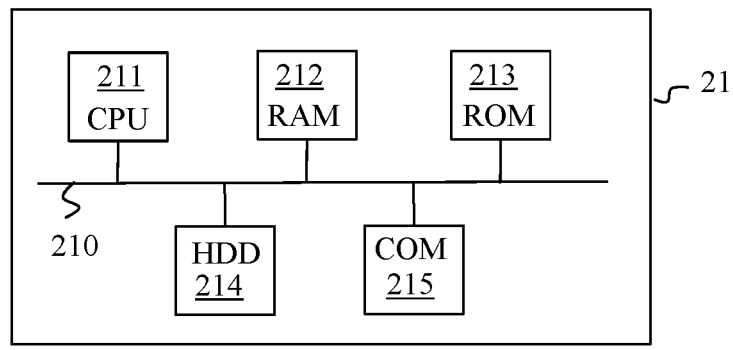
FIG. 3 illustrates schematically an example of hardware architecture of a processing module implementing the method for detecting the presence of a body part carrying an imprint.

FIG. 3 illustrates schematically an example of hardware architecture of the processing module 21.

According to the example of hardware architecture shown in FIG. 3, the processing module 21 then comprises, connected by a communication bus 210: a processor or CPU (central processing unit) 211; a random access memory (RAM) 212; a read only memory (ROM) 213; a storage unit such as a hard disk or a storage medium reader, such as an SD (secure digital) card reader 214; at least one communication interface 215 enabling the processing module 21 to communicate with the fingerprint sensor 20 and the controller.

The processor 211 is capable of executing instructions loaded into the RAM 212 from the ROM 213, from an external memory (not shown), from a storage medium (such as an SD card), or from a communication network. When the analysis module 21 is powered up, the processor 211 is capable of reading instructions from the RAM 212 and executing them. These instructions form a computer program causing the implementation, by the processor 211, of the method described in relation to FIG. 4.

Figure 4:
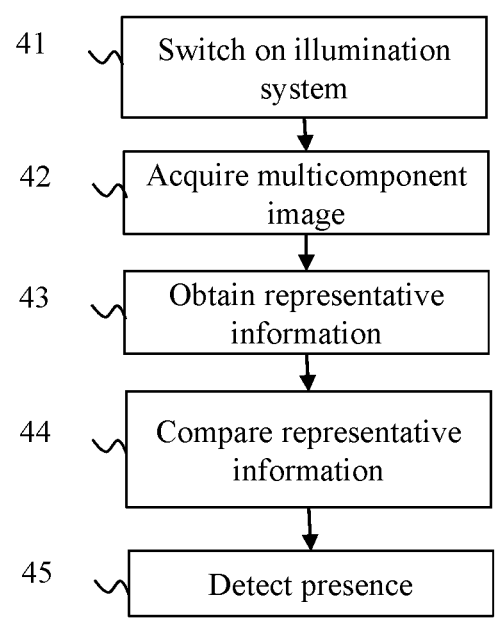
FIG. 4 illustrates schematically an example of a method for detecting the presence of a body part carrying an imprint.

The method described in relation to FIG. 4 may be implemented in software form by the execution of a set of instructions by a programmable machine, for example a DSP (digital signal processor), a microcontroller or a GPU (graphics processing unit), or be implemented in hardware form by a machine or a dedicated component, for example an FPGA (field-programmable gate array) or an ASIC (application-specific integrated circuit).

It should be noted that the processing module 21 could just as well have been included in the fingerprint sensor 20.

FIG. 4 illustrates schematically an example of a method for detecting the presence of a body part carrying a fingerprint.

In a step 41, the processing module 21 triggers the switching on of at least one of the light sources 101A or 101B of the fingerprint sensor 20. In one embodiment, when a user places a finger on the fingerprint sensor 20, he presses on a button to trigger the switching on.

In a step 42, the processing module 21 triggers an acquisition of a multicomponent image by the image sensor 102. In one embodiment, the image sensor 102 comprises a matrix of pluralities of photoreceivers, each plurality comprising at least three photoreceivers capturing different predetermined wavelength ranges. Each pixel of an image generated by the image sensor 102 comprising a plurality of components, each component is supplied by at least one of the photoreceivers in the plurality associated with this pixel. In one embodiment, each plurality comprises four photoreceivers, two photoreceivers capture light rays in a wavelength range corresponding to the green and supplying a green component, one photoreceiver captures light rays in a wavelength range corresponding to the blue and supplying a blue component, and one photoreceiver captures light rays in a wavelength range corresponding to the red and supplying a red component.

In a step 43, the processing module 21 obtains, for each colour component of the multicomponent image, information representative of a signal generated by said image sensor for said colour component.

In a step 44, the processing module 21 compares said representative items of information with each other and, in a step 45, detects the presence of a body part according to a result of the comparison.

We describe hereinafter in relation to FIGS. 5A, 5B and 5C detailed embodiments of steps 43, 44 and 45.

Figure 5A:
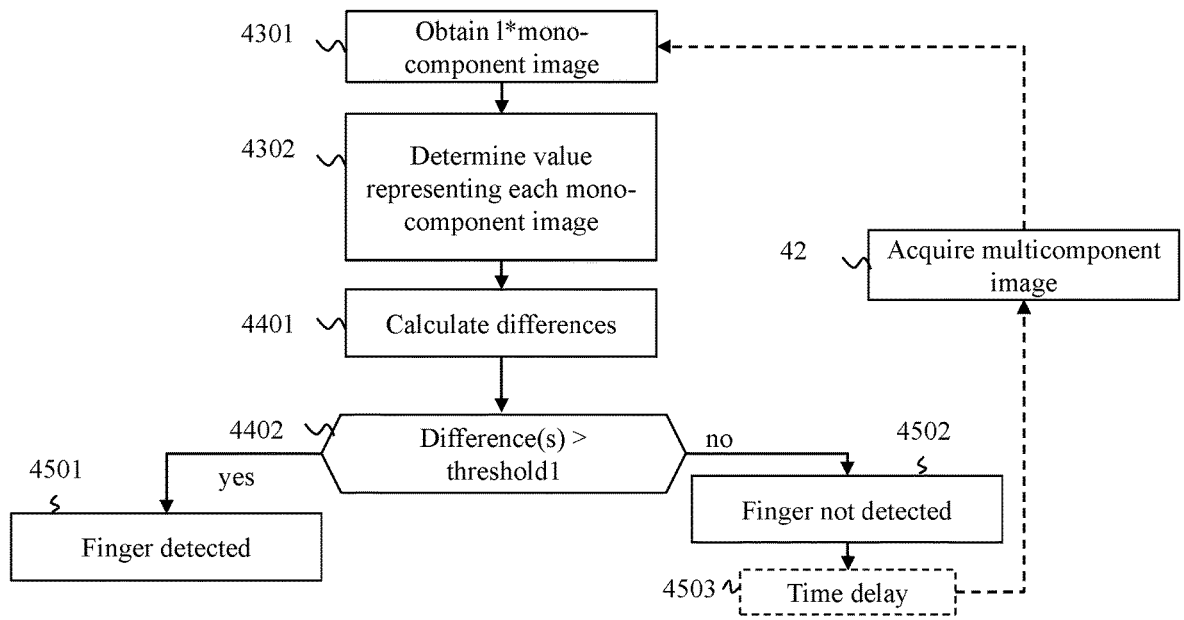
FIG. 5A illustrates schematically a detail of a first particular implementation of the method for detecting the presence of a body part carrying an imprint.

FIG. 5A illustrates schematically a detail of a first particular implementation of the method for detecting the presence of a body part carrying a fingerprint.

In the implementation described in relation to FIG. 5A, the fingerprint sensor 20 functions according to the total reflection with dark-field principle and the light source generates light the wavelengths of which lie solely in one of the predefined wavelength ranges, referred to as the illumination wavelength range.

In a step 4301, the processing module 21 forms a mono-component image from each component of the multicomponent image. If for example each pixel of the multicomponent image comprises a red component, a green component and a blue component, the processing module forms a mono-component image comprising the red component, a mono-component image comprising the green component and a mono-component image comprising the blue component.

In a step 4302, the processing module 21 determines a value representing each mono-component image. In one embodiment, for each mono-component image, the processing module 21 calculates a dynamic value in each pixel of the image. To do this, for each pixel of a mono-component image, the processing module 21 defines a neighbourhood around said pixel, for example in the form of a square matrix with predefined sides centred on said pixel, and calculates a value of local dynamic in the form of an average of the values of the pixels included in this neighbourhood. In one embodiment, the side of the square matrix is ten pixels. Once all the pixels of the mono-component image have been run through, the processing module calculates an average of the values of the local dynamics of the whole of the image in order to obtain a global dynamic value of the mono-component image. The value of the global dynamic of a mono-component image forms a value representing said mono-component image.

Steps 4301 and 4302 detail step 43.

In a step 4401, the processing module 21 calculates a difference between the values representing each mono-component image taken in pairs. When the multicomponent image comprises three components (red, green, blue), the processing module 21 calculates three differences.

It is known that a finger placed on the fingerprint sensor 20 will generate an image mainly in the component corresponding to the wavelength range emitted by the light source whereas a latent illuminated by an ambient light generates an image in each component. Thus, if the value representing a component corresponding to the wavelength range emitted by the light source is very different from the other representative values, it can be deduced from this that a finger is placed on the fingerprint sensor 20. On the other hand, if all the representative values are approximately equal, it can be deduced from this that no finger is placed on the fingerprint sensor.

In a step 4402, each difference calculated is compared with a first predetermined threshold. The first predetermined threshold represents a high difference beyond which the probability of the fingerprint sensor 20 being in the presence of a finger is very high and has for example been determined by activating the fingerprint sensor 20 of the implementation in FIG. 5 on a wide panel of fingers and on latents left on the fingerprint sensor 20 by said fingers.

Steps 4401 and 4402 are a detail of step 44.

In a step 4501, when the difference between the representative value determined for the colour component corresponding to the illumination wavelength range and the other representative values is higher than the first predetermined threshold, the processing module 21 determines that the fingerprint sensor 20 is in the presence of a finger.

Otherwise the processing module 21 determines, during a step 4502, that the fingerprint sensor 20 is not in the presence of a finger.

When the difference between the representative value determined for the colour component corresponding to the illumination wavelength range and the other representative values is higher than the first predetermined threshold, the probability that the fingerprint sensor 20 is in the presence of a finger is very high. On the other hand, when the difference between the representative value determined for the colour component corresponding to the illumination wavelength range and the other representative value is lower than the first predetermined threshold, it cannot with certainty be concluded that the fingerprint sensor 20 is not in the presence of a finger. This is because the characteristics of the multicomponent image acquired during step 42 are dependent on the state of the finger at the moment of this acquisition and may change over time. Thus a finger that is dry at the time of the acquisition of the multicomponent image may, little by little, become moist and thus allow acquisition of a more usable multicomponent image.

In one embodiment, following step 4502, the processing module 21 implements an optional time-delay step 4503. During this step, the processing module 21 waits for a predefined period of a few milliseconds (for example 10 milliseconds), implements step 42 again and then returns to step 4301 so as to implement the algorithm of FIG. 5A again. The processing module 21 can thus loop back onto the algorithm in FIG. 5A a predefined number of times N (N is for example equal to 5). If during one of the implementations of step 4402, the difference between the representative value determined for the colour component corresponding to the illumination wavelength range and the other representative values is higher than the first predetermined threshold, the processing module 21 determines that the fingerprint sensor 20 is in the presence of a finger and the execution of the method described in relation to FIG. 5A stops. If after N loops no finger is detected, the processing module 21 considers definitively that there are no fingers on the fingerprint sensor 20.

Steps 4501, 4502 and 4503 are a detail of step 45.

Figure 5B:
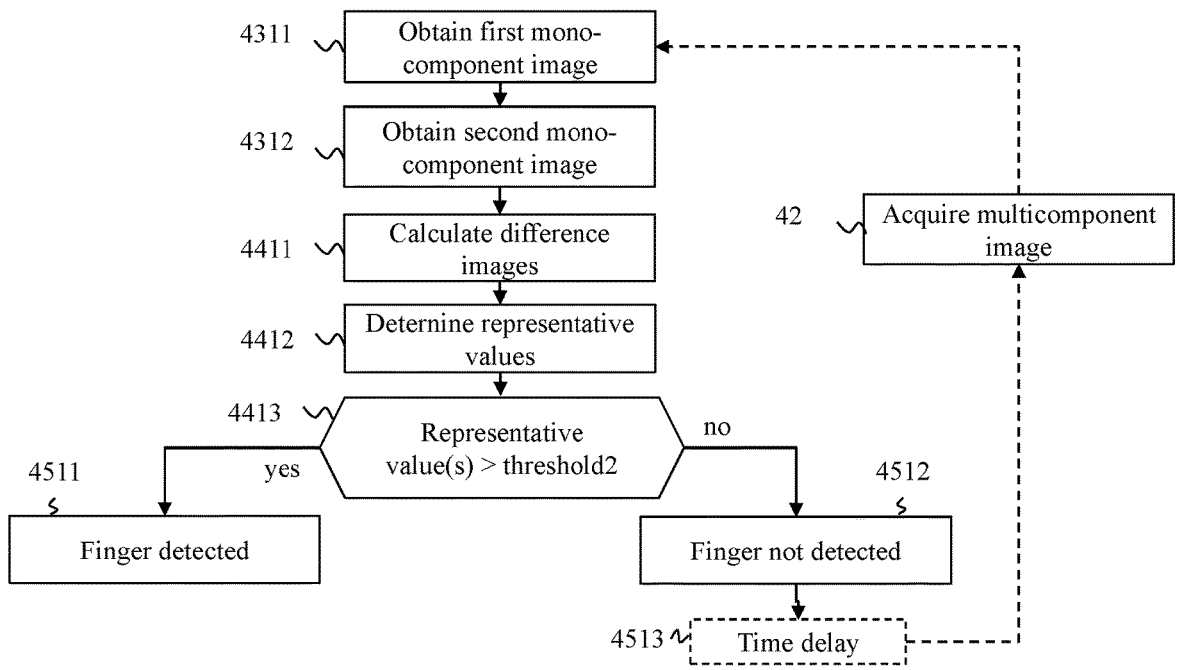
FIG. 5B illustrates schematically a detail of a second particular embodiment of the method for detecting the presence of a body part carrying an imprint.

FIG. 5B illustrates schematically a detail of a second particular implementation of the method for detecting the presence of a body part carrying a fingerprint.

In the implementation described in relation to FIG. 5B, the fingerprint sensor 20 functions according to the total reflection with dark-field principle and the light source produces light the wavelengths of which are situated in a first predefined wavelength range and in at least one second predefined wavelength range.

In a step 4311, the processing module 21 obtains, from the multicomponent image, a first mono-component image comprising the component of the multicomponent image corresponding to the first predefined wavelength range.

In a step 4312, the processing module 21 obtains from the multicomponent image, for each second predefined wavelength range, a second mono-component image comprising the component of the multicomponent image corresponding to said second predefined wavelength range.

In this embodiment, the first mono-component image and each second mono-component image constitute the information representing a signal generated by said image sensor for each component.

Steps 4311 and 4312 are a detail of step 43.

In a step 4411, the processing module 21 calculates a difference between each mono-component image taken in pairs. If the processing module 21 has obtained three mono-component images, it then obtains three difference images.

When a finger is placed on the fingerprint sensor 20, the spectral response of said finger means that at least one of the differences between two components is significant. The spectral response of a latent is different since, in this case, each difference is small.

In a step 4412, the processing module 21 calculates a global dynamic value as described in relation to step 4302, for each mono-component image.

In a step 4413, each global dynamic value is compared with a second predetermined threshold. The second predetermined threshold represents a significant difference beyond which the probability of the fingerprint sensor 20 being in the presence of a finger is very high and has for example been determined by activating the fingerprint sensor 20 of the implementation in FIG. 5B on a wide panel of fingers and on latents left on the fingerprint sensor 20 by said fingers.

Steps 4411, 4412 and 4413 are a detail of step 44.

When at least one difference is greater than the second threshold, the processing module 21 considers, during a step 4511, that the fingerprint sensor 20 is in the presence of a finger. Otherwise the processing module 21 considers, during a step 4512, that the fingerprint sensor 20 is not in the presence of a finger.

Steps 4511 and 4512 correspond to a detail of step 45.

In one embodiment, following step 4512, the processing module 21 implements an optional step 4513 identical to step 4503 and loops back onto the algorithm in FIG. 5B a predefined number of times as described in relation to FIG. 5A.

In one embodiment, the first predefined wavelength range corresponds to the red and a second predefined wavelength range corresponds to the green or blue.

Figure 5C:
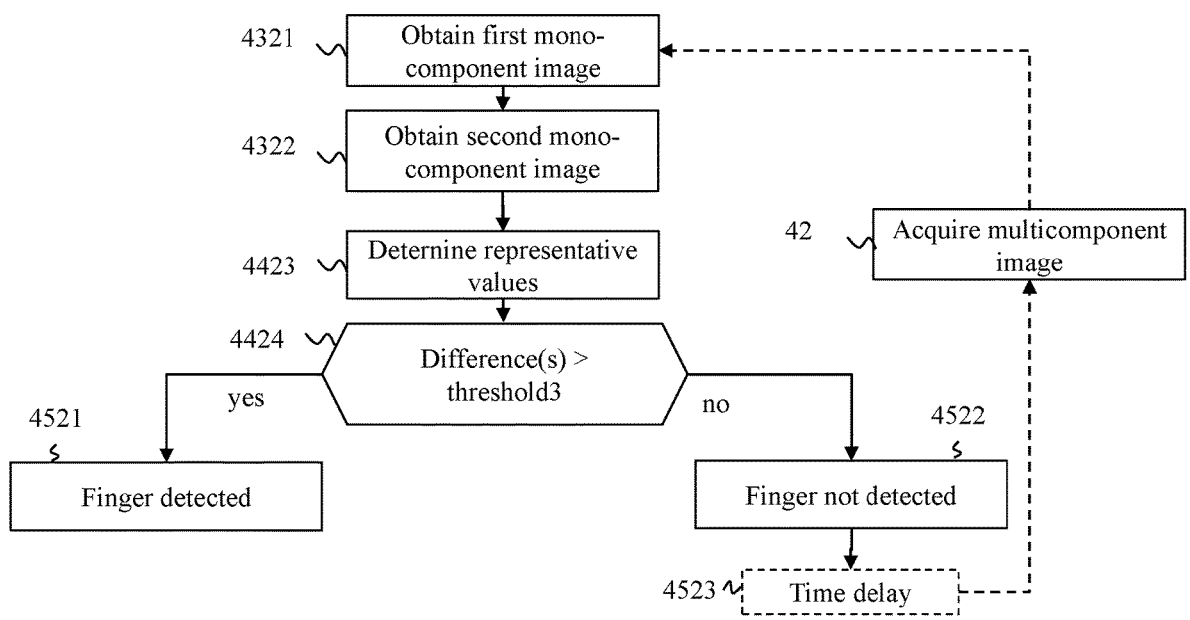
FIG. 5C illustrates schematically a detail of a third particular implementation of the method for detecting the presence of a body part carrying an imprint.

FIG. 5C illustrates schematically a detail of a third particular implementation of the method for detecting the presence of a body part carrying a fingerprint.

In the implementation described in relation to FIG. 5C, the fingerprint sensor 20 functions according to the total reflection with light-field principle and the light source produces a light the wavelengths of which are situated in a first predefined wavelength range and at least a second predefined wavelength range. It is assumed that the first predefined wavelength range corresponds to the red and that a second predefined wavelength range corresponds to the green or blue. It is known that a finger absorbs light differently according to the wavelength thereof. Thus the absorption is greater for blue light and for green light than for red light. Consequently an image sensor of a fingerprint sensor receives fewer light rays corresponding to the green and blue wavelengths than light rays corresponding to the red when a finger is placed on the sensor. On the other hand, the absorption by a latent is the same whatever the wavelength. If a monocomponent image corresponding to the green (or blue) comprises less information than a monocomponent image corresponding to the red, it can be deduced from this that the fingerprint sensor 20 is in the presence of a finger. If the information contained in each monocomponent image is identical, it can be deduced from this that the fingerprint sensor 20 is not in the presence of a finger.

The implementation in FIG. 5C begins with steps 4321 and 4322 identical to steps 4311 and 4312.

In a step 4423, the processing module 21 calculates information representing each mono-component image. In one embodiment, the processing module 21 calculates a global dynamic value as described in relation to step 4302 for each mono-component image.

In a step 4424, the processing module 21 compares the information representing the mono-component image corresponding to the red with the information representing the mono-component image corresponding to the green and/or the information representing the mono-component image corresponding to the blue.

If a difference between the information representing the mono-component image corresponding to the red and the information representing the mono-component image corresponding to the green and/or blue is above a third threshold, the processing module 21 considers that the fingerprint sensor 20 is in the presence of a finger in a step 4521. Otherwise the processing module 21 considers that the fingerprint sensor 21 is not in the presence of a finger in a step 4522.

The third predetermined threshold represents a significant difference beyond which the probability of the fingerprint sensor 20 being in the presence of a finger is very high and has for example been determined by activating the fingerprint sensor 20 of the implementation in FIG. 5C on a wide panel of fingers and on latents left on the fingerprint sensor 20 by said fingers.

Steps 4423 and 4424 are details of step 44.

Steps 4521 and 4522 are details of step 45.

In one embodiment, following step 4522, the processing module 21 implements an optional step 4523 identical to step 4503 and loops back onto the algorithm described in relation to FIG. 5C just like what is done in the algorithm in FIG. 5A.

In one embodiment, the image sensor 102 successively provides mono-component images each corresponding to a predefined wavelength range, the mono-component images forming the multicomponent image.

The invention claimed is:

1. A method for detecting the presence of a body part carrying an imprint on an imprint sensor comprising a transparent face on which a body part must be placed, an image sensor, situated opposite the transparent face, able to acquire an image of an imprint, a light source for illuminating a body part placed on the transparent face, the imprint sensor functioning according to a total reflection with darkfield principle and the light source producing light the wavelengths of which are situated in a first predefined wavelength range, in a second predefined wavelength range, and in a third predefined wavelength range, wherein the method comprises:

switching on the light source;

obtaining a multicomponent image from the image sensor, each color component of the multicomponent image corresponding to a predefined wavelength range;

obtaining, for each color component of said multicomponent image, an item of information representing a signal generated by said image sensor for said color component; and wherein obtaining, for each color component of said multicomponent image, an item of information representative of a signal generated by said image sensor for said color component comprises:

obtaining from the image sensor a first mono-component image comprising the component of the multicomponent image corresponding to the first predefined wavelength range, a second mono-component image comprising the component of the multicomponent image corresponding to the second predefined wavelength range and a third mono-component image comprising the component of the multicomponent image corresponding to the third predefined wavelength range, each mono-component image being an item of information representing a signal generated by said image sensor for a color component; and wherein said method further comprises:

calculating a first difference image by subtracting pixel by pixel the first mono-component image from the second mono-component image, a second difference image by subtracting pixel by pixel the first mono-component image from the third mono-component image and a third difference image by subtracting pixel by pixel the second mono-component image from the third mono-component image;

calculating, for each pixel of each difference image, a value of local dynamic being an average of the values of the pixels included in a neighborhood of said pixel;

calculating, for each difference image, a global dynamic value being an average of the values of local dynamic on the whole difference image, and comparing each of the three global dynamic values with a predetermined threshold and detecting the presence of a body part when at least one of the three global dynamic values is above said predetermined threshold.

2. The method according to claim 1, wherein the first component is a red component and the second component is a green component and the third component is a blue component.

3. A non-transitory information storage medium, storing a computer program comprising program code instructions which, when executed by a programmable device, causes said programmable device to implement the method according to claim 1.

4. A device for detecting the presence of a body part carrying an imprint on an imprint sensor comprising a transparent face on which a body part must be placed, an image sensor, situated opposite the transparent face, able to acquire an image of an imprint, and a light source for illuminating a body part placed on the transparent face, the imprint sensor functioning according to a total reflection with dark-field principle and the light source producing light the wavelengths of which are situated in a first predefined wavelength range, in a second predefined wavelength range, and in a third predefined wavelength range, wherein the device comprises electronic circuitry adapted for:

switching on the light source;

obtaining a multicomponent image from the image sensor, each color component of the multicomponent image corresponding to a predefined wavelength range;

obtaining, for each color component of said multicomponent image, an item of information representative of a signal generated by said image sensor for said color component;

wherein obtaining, for each color component of said multicomponent image, an item of information representative of a signal generated by said image sensor for said color component comprises:

obtaining from the image sensor a first mono-component image comprising the component of the multicomponent image corresponding to the first predefined wavelength range, a second mono-component image comprising the component of the multicomponent image corresponding to the second predefined wavelength range and a third mono-component image comprising the component of the multicomponent image corresponding to the third predefined wavelength range, each mono-component image being an item of information representing a signal generated by said image sensor for a color component; and wherein said electronic circuitry is further adapted for:

calculating a first difference image by subtracting pixel by pixel the first mono-component image from the second mono-component image, a second difference image by subtracting pixel by pixel the first mono-component image from the third mono-component image and a third difference image by subtracting pixel by pixel the second mono-component image from the third mono-component image;

calculating, for each pixel of each difference image, a value of local dynamic being an average of the values of the pixels included in a neighborhood of said pixel;

calculating, for each difference image, a global dynamic value being an average of the values of local dynamic on the whole difference image, and comparing each of the three global dynamic values with a predetermined threshold and detecting the presence of a body part when at least one of the three global dynamic values is above said predetermined threshold.

5. Imprint sensor comprising a device according to claim 4.

* * * * *